United States Patent [19]
Demus et al.

[11] Patent Number: 4,961,876
[45] Date of Patent: Oct. 9, 1990

[54] LIQUID CRYSTALLINE FERROELECTRIC DERIVATIVES OF BRANCHED ACYCLIC ALPHA-CHLOROCARBOXYLIC ACIDS

[75] Inventors: Dietrich Demus; Horst Zaschke, both of Halle; Wolfgang Weissflog, Halle-Neustadt; Kristina Mohr, Halle-Neustadt; Saskia Köhler, Halle-Neustadt; Kerstin Worm, Halle, all of German Democratic Rep.

[73] Assignee: VEB Werk fuer Fernsehelektronik im VEB Kombinat Mikroelektronik, Berlin, German Democratic Rep.

[21] Appl. No.: 245,962

[22] Filed: Sep. 15, 1988

Related U.S. Application Data

[63] Continuation of Ser. No. 898,284, Aug. 20, 1986, abandoned.

[30] Foreign Application Priority Data

Aug. 26, 1985 [DD] German Democratic Rep. .................... 2799446
Aug. 26, 1985 [DD] German Democratic Rep. .................... 2799454

[51] Int. Cl.$^5$ .............................................. C09K 19/20
[52] U.S. Cl. .......................... 252/299.67; 252/299.01; 299.65, 299.66, 299.67, 299.68; 350/350 S
[58] Field of Search ............................. 560/141, 145; 252/299.01, 299.6, 299.61, 299.63, 299.64, 299.65, 299.66, 299.67, 299.68; 350/350 S,

[56] References Cited

U.S. PATENT DOCUMENTS 3,790,498  2/1974  Katagiri et al. ................. 252/299.67
4,576,732  3/1986  Isogai et al. .................... 252/299.65
(List continued on next page.)

FOREIGN PATENT DOCUMENTS 136725   4/1985  European Pat. Off. ....... 252/299.67
164814  12/1985  European Pat. Off. ....... 252/299.65
248335   5/1987  European Pat. Off. . .
3515374 11/1956  Fed. Rep. of Germany ......................... 252/299.61
86/174294 8/1986 Japan .............................. 252/299.67
87/111950 5/1987 Japan .............................. 252/299.65

OTHER PUBLICATIONS

Goodby et al., Liquid Crystals & Ordered Fluids, vol. 4, pp. 1-32 (1984).

*Primary Examiner*—John S. Maples
*Assistant Examiner*—Richard Treanor
*Attorney, Agent, or Firm*—Jordan and Hamburg

[57] ABSTRACT

Liquid crystalline ferroelectric derivatives of branched acyclic alpha-chlorocarboxylic acids of the general formula I

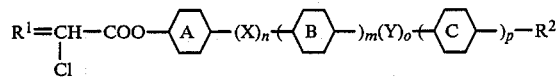

wherein
n=0 or 1; m=0 or 1, o=0 or 1; p=0 or 1
X= —COO—, —OOC—, or —CH$_2$—CH$_2$—
Y=X, —CH$_2$—, —N=N—, or —N=N(O)—,

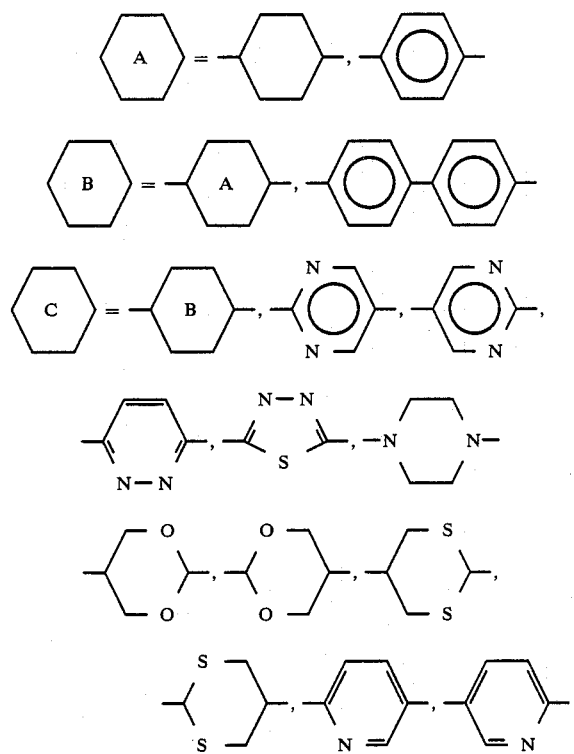

R$^1$ = (CH$_3$)$_2$CH—, (CH$_3$)$_2$CH—CH$_2$—, or C$_2$H$_5$—CH(CH$_3$)—

R$^2$ = C$_l$H$_{2l+1}$, —O—C$_l$H$_{2l+1}$, —S—C$_l$H$_{2l+1}$, —CO—C$_l$H$_{2l+1}$, —OOC—C$_l$H$_{2l+1}$, —COO—C$_l$H$_{2l+1}$, or —NH—C$_l$H$_{2l+1}$ l = 1-12.

It was discovered that, by reacting chiral alpha-chlorocarboxylic acids or alpha-chlorocarboxylic acid chlorides or bromides, synthesized from natural alpha-amino acids by reaction with nitric and hydrochloric acids, with appropriate hydroxy compounds directly or in the presence of strongly dehydrating substances, preferably carbodiimides, liquid crystalline ferroelectric substances of the general formula I are formed.

The inventive substances by themselves, in mixtures with one another as well as with other liquid crystalline substances or substances which are not liquid crystalline, can form liquid crystalline ferroelectric phases, which make them suitable for use in displays.

8 Claims, No Drawings

U.S. PATENT DOCUMENTS

| | | | |
|---|---|---|---|
| 4,592,858 | 6/1986 | Huguchi et al. | 252/299.66 |
| 4,596,667 | 6/1986 | Inukai et al. | 252/299.67 |
| 4,613,209 | 9/1986 | Goodby et al. | 350/350 S |
| 4,614,609 | 9/1986 | Inoue et al. | 252/299.66 |
| 4,643,842 | 2/1987 | Tagachi et al. | 252/299.67 |
| 4,695,650 | 9/1987 | Walba et al. | 252/299.67 |
| 4,695,651 | 9/1987 | Higuchi et al. | 252/299.66 |
| 4,728,458 | 3/1988 | Higuchi et al. | 252/299.65 |
| 4,820,839 | 4/1989 | Krause et al. | 252/299.61 |
| 4,867,903 | 9/1989 | Nohira et al. | 252/299.67 X |
| 4,874,545 | 10/1989 | Heppke et al. | 252/299.67 X |
| 4,886,623 | 12/1989 | Mitsuhashi et al. | 252/299.67 X |

LIQUID CRYSTALLINE FERROELECTRIC DERIVATIVES OF BRANCHED ACYCLIC ALPHA-CHLOROCARBOXYLIC ACIDS

This application is a continuation of application Ser. No. 898,284, filed Aug. 20, 1986, now abandoned.

SUMMARY OF THE INVENTION

It has now been discovered that liquid crystalline ferroelectric derivatives of branched acyclic alpha-chlorocarboxylic acids of the general formula

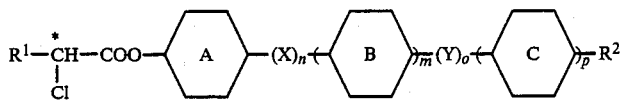

I n = 0,1; m = 0,1; o = 0,1; p = 0,1

X = —COO—, —OOC—, —$CH_2$—$CH_2$—

Y = X, —$CH_2$—, —N=N—, —N=N(O)—

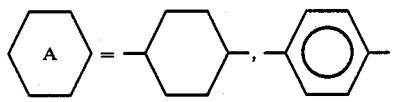

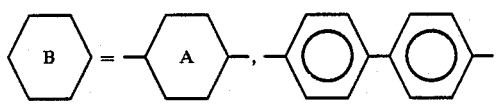

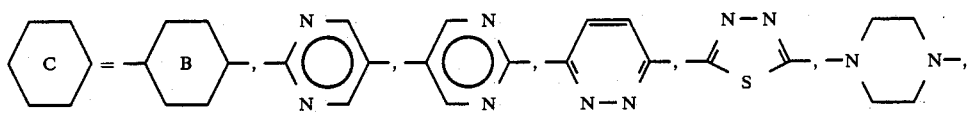

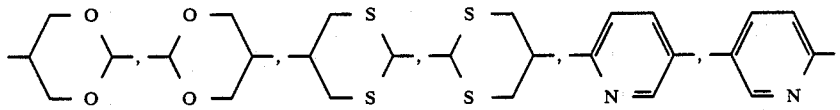

$R^1$ = $(CH_3)_2CH$—, $(CH_3)_2CH$—$CH_2$—, $C_2H_5$—$CH(CH_3)$—

$R^2$ = —$C_lH_{2l+1}$, —O—$C_lH_{2l+1}$, —S—$C_lH_{2l+1}$, —CO—$C_lH_{2l+1}$, —OOC—$C_lH_{2l+1}$, —COO—$C_lH_{2l+1}$, —NH—$C_lH_{2l+1}$ l = 1–12, chemical influences, have low melting points and show sufficiently high dipole moments.

BACKGROUND OF THE INVENTION AND RELATED ART STATEMENT

The invention relates to novel liquid crystalline ferroelectric derivatives of branched acyclic alpha-chlorocarboxylic acids.

Liquid crystalline ferroelectric compounds are described in the literature. They are optically active compounds, which are predominantly derivatives of the optically active amyl alcohols and optically active alpha-chloropropanols (P. Keller, S. Juge, L. Liebert, L. Strzelecki: C.R. Acad. Sci., Ser. 282 C, 639 (1976); P. Keller: Ann. Phys. 139–44 (1978); M. V. Loseva, B. I. Ostrowskii, A. Z. Rabinovich, A. S. Sonin, B. A. Strukov, N. I. Chernova: Pis'ma Zh. Eksp. Teor. Fiz. 28, 404 (1978); A. Hallsby, M. Nilsson, B. Otterholm: Mol. Cryst. Liq. Cryst. 82, 61–8 (1982); P. Keller: Ferroelectrics 1984; J. W. Goodby, T. M. Leslie: Mol. Cryst. Liq. Cryst. 110, 175 (1984). However, when used in displays with memory properties, these substances have a series of disadvantages, such as very high melting temperatures, instability towards heat, light or chemical influences or very low dipole moments, which bring about low values for the spontaneous polarization.

It is an object of the invention to find substances, which exhibit good stability towards heat, light and are suitable for depicting numerals, symbols and illustrations in rapidly switching displays in optoelectronics.

The inventive liquid crystalline ferroelectric derivatives of branched acyclic alpha-chlorocarboxylic acids are obtained by the reaction of chiral alpha-chlorocarboxylic acids or alpha-chlorocarboxylic acid chlorides or bromides, synthesized from natural amino acids by reaction with nitric acid and hydrochloric acid, with appropriate hydroxy compounds directly or in the presence of strongly dehydrating substances, preferably carbodiimides such as dicyclohexylcarbodiimide, 1-(3-dimethylaminopropyl)-3-ethyl-carbodiimide methiodide or 1-(3-dimethylaminopropyl)-3-ethyl-carbodiimide-metho-p-toludisolfonate.

The alpha-chlorocarboxylic acid chlorides are esterified with the appropriate hydroxy compounds by the Schotten-Baumann or von Einhorn method.

As alpha-chlorocarboxylic acids, preferably the derivatives, obtained from the natural amino acids L-valine, L-leucine and L-isoleucine by reaction with nitric acid and hydrochloric acid, are suitable. However, the chlorocarboxylic acids, obtainable from the optically active antipodes D-valine, D-leucine and D-isoleucine, can also be used. These compounds can be synthesized according to known procedures, for example, see E. FISCHER, H. SCHEIBLER: Ber. Dtsch. Chem. Ges. 41, 889 (1908); P. KARRER, M. RENHARD: J. Biol. Chem. 28, 497 (1946); P. KARRER, H. RESCHOFSKY, W. KAASE: Helv. Chim. Acta 30, 271 (1947).

The hydroxy compounds are fragments of liquid crystalline substances, which themselves do not have to be liquid crystalline and can be synthesized according to known procedures (cf. references in D. Demus and H. Zaschke "Flüssige Kristalle in Tabellen II" (Liquid Crystals In Tables II), Leipzig, 1984). In the process, the chirality of the alpha-chlorocarboxylic grouping is retained and, surprisingly, the yield, when the process is carried out by reacting alpha-chlorocarboxylic acids with the hydroxy compounds in the presence of strongly dehydrating agents, is approximately twice as high (40–60%) as when the process is carried out by first of all reacting to form the alpha-chlorocarboxylic acid chlorides and subsequently esterifying. The substances are colorless, chemically and thermally very stable and, due to the chloro substituent directly at the chiral center, have a high dipole moment and, with that, a high spontaneous polarization.

DETAILED DESCRIPTION OF PREFERRED EMBODIMENTS

The invention is explained in greater detail in the following by means of synthesis examples.

EXAMPLE 1

(S)-(+)-1-(4-n-Alkoxy-benzoyloxy)-4-(2-chloro-3-methylbutyryloxy)-biphenyls

A. (S)-(+)-2-chloro-3-methylbutyric acid

L-(+)-valine (10 g, 0.085 moles), 1 g urea, 30 mL concentrated hydrochloric acid and 15 mL concentrated nitric acid are shaken for about 30–60 minutes in a flask, until the evolution of nitrogen has ended. After that, the reaction batch is heated for 45 minutes at 70° to 80° C. in a water bath (complete dissolution with foaming, separation of a yellow oil). After cooling, the mixture is extracted with ether, the ether extract is washed several times with cold water, dried over calcium chloride, the solvent is evaporated off in a rotary evaporator and the residue is fractionally distilled under vacuum.

Yield: 3.2 g (28% of the theoretical).
Boiling point: 125°–126° C./4.25 kPa.

B. (S)-(+)-2-Chloro-3-methylbutyryl chloride (S)-(+)-2-chloro-3-methylbutyric acid (20 g, 0.147 moles) and 13 g $PCl_3$ are shaken for 12 hours in a flask and subsequently heated for 1 hour on the water bath. The reaction mixture is distilled at atmospheric pressure.

Yield: 5.4 g (27% of the theoretical).
Boiling point 144°–146° C.

If, as halogen transferring agent, a 5-fold amount of $SOCl_2$ is used and the batch is heated for 2 hours at 50° to 60° C. on the water bath, 12.2 g of (S)-(+)-2-chloro-3-methylbutyryl chloride (60% of the theoretical amount) are obtained.

C.
(S)-(+)-1-(4-n-Alkoxy-benzoyloxy)-4-(2-chloro-3-methylbutyryloxy)biphenyls

To the solution of 0.005 moles of 1-(4-n-alkoxy-benzoyloxy)-4-hydroxy-biphenyl, 0.6 mL of triethylamine and 50 mL of absolute toluene, 0.77 g (0.005 moles) of (S)-(+)-2-chloro-3-methyl-butyryl chloride are added. The mixture is allowed to stand for a day at room temperature and subsequently heated for 1 hour at 80° C. on the water bath. After filtering off the precipitate formed, the solvent is distilled off and the residue is recrystallized several times from ethanol/water. The yields are 50 to 60% of the theoretical. The liquid crystalline melting behavior is given in the Tables.

EXAMPLE 2

(S)-(+)-1-(4-n-Alkoxy-benzoyloxy)-4-(4-(2-chloro-3-methylbutyryloxybenzoyloxy)-benzene A. (S)-(+)-4-(2-chloro-3-methyl-butyryloxy)-benzoic acid 4-Hydroxybenzoic acid (8.9 g, 0.065 moles) is dissolved in 20 mL of absolute pyridine and 10 g (0.065 moles) of (S)-(+)-2-chloro-3-methylbutyryl chloride are added dropwise with stirring at 0° to 5° C. The mixture is allowed to stand for 4 hours at room temperature and then poured onto ice/conc. HCl (200 g/30 mL). The precipitate is filtered off with suction and washed several times with dilute HCl and water. The residue is recrystallized from methanol/water.

Yield: 11.7 g (70% of the theoretical).
Melting point: 150°–151° C.

B.
(S)-(+)-1-(4-n-alkoxy-benzoyloxy)-4-(4-(2-chloro-3-methyl-butyryloxy)-benzoyloxy)-benzene To 0.003 moles of 1-(4-n-alkyloxy-benzoyloxy)-4-hydroxybenzene, dissolved in 30 mL of toluene and 0.6 mL (0.004 moles) of triethylamine, (S)-(+)-4-(2-chloro-3-methyl-butyryloxy)-benzoyl chloride, synthesized by reacting 0.8 g (0.003 moles) of (S)-(+)-4-(2-chloro-3-methyl-butyryloxy)-benzoic acid with 3 mL $SOCl_2$, is added dropwise as crude product. The mixture is allowed to stand for 1 day at room temperature and then heated briefly to 80° C. (water bath temperature). Subsequently, the precipitate is filtered off, the mother liquor is concentrated and the residue remaining is recrystallized several times from ethanol/water.

The yields are 55 to 60% of the theoretical amount.

EXAMPLE 3

(S)-(+)-1-(4-n-Alkoxy-benzoyloxy)-4-(4-(2-chloro-3-methyl-pentanoyloxy)-benzoyloxy)-benzene A. (S)-2-Chloro-3-methylpentanoic acid To 20 g (0.150 moles) of L-(+)-isoleucine and 2 g of urea, 60 mL concentrated HCl and 30 mL concentrated $HNO_3$ are added at room temperature. The mixture is subsequently heated for 1 hour at 80° C. and then for 1 hour at 50° C. on a water bath (complete dissolution of the acid with heavy foaming). After cooling, the solution is extracted with ether several times, the ether extract is washed with water and dried over calcium chloride, the solvent is distilled off in a rotary evaporator and the residue is fractionated under vacuum.

Yield: 6.7 g (29% of the theoretical)
Boiling point: 136°–139° C./3.47 kPa

EXAMPLE 4

A. (S)-2-Chloro-4-methyl-pentanoic acid

L-(+)-Leucine (10 g, 0.076 moles) is mixed with 24 mL of concentrated HCl and 10 mL of concentrated $HNO_3$ with the addition of 2 g of urea and subsequently heated for 1 hour at 80° C. and then for 1 hour at 50° C. on a water bath (complete dissolution of the acid with heavy foaming). After cooling, the solution is extracted with ether several times, the ether extract is washed with water and dried over calcium chloride, the solvent is distilled off in a rotary evaporator and the residue is fractionally distilled under vacuum.

Yield: 4.1 g (36% of the theoretical).
Boiling point: 136°–137° C., 3.99 kPa.

B. Esterification in the Presence of Dicyclohexylcarbodiimide (DCC)

While stirring, 1.5 g (0.01 moles) of (S)-2-chloro-3-methylpentanoic acid, 2.06 g (0.01 moles) of DCC, 0.12 g (0.001 moles) of 4-dimethylaminopyridine (DMAP) and an amount of 1-(4-n-alkoxy-benzoyloxy)-4-hydroxy-benzene corresponding to 0.01 moles are added to 50 mL of ether. The mixture is allowed to stand 2–3 days at room temperature. The N,N'-dicyclohexylurea formed is then filtered off with suction. The mother liquor is washed several times with water and dried over sodium sulfate. The solvent is then distilled off in a rotary evaporator and the residue is recrystallized several times from methanol.

Yield: 40–50% of the theoretical.

C. Esterification in the Presence of Water-Soluble Carbodiimide

To a solution of 0.3 g (0.0021 moles) of (S)-2-chloro-3-methylpentanoic acid, 0.003 moles of 1-(4-n-alkyloxy-benzoyloxy)-4-hydroxybenzene and 0.01 g DMAP in 50 mL of absolute $CH_2Cl_2$ in a flask, 0.69 g (0.0025 moles) of 1-(3-dimethylaminopropyl)-3-ethyl-carbodiimide tosylate in 30 mL of absolute $CH_2Cl_2$ is added dropwise with stirring and cooling in ice. After standing for 2–3 days at room temperature, the reaction batch is washed several times with water and dried over sodium sulfate. The solvent is then evaporated off in a rotary evaporator and the residue is recrystallized several times from n-hexane/acetic acid.

Yield: 50–60% of the theoretical

The following Tables 1–6 show the transition temperatures of inventive substances.

In the Tables:
K = the crystalline, solid state
$S_C$ = the ferroelectric smectic C phase
$S_A$, $S_B$, $S_G$ = Smectic A, B, G phases
CH = cholesterinic phase
Is = isotropic liquid phase
N = nematic phase
The temperatures are given in °C.

TABLE 1

$(CH_3)_2CH-\overset{*}{C}H-COO-\phenyl-COO-\phenyl-OOC-\phenyl-OC_nH_{2n+1}$
        |
        Cl

| n | K |   | $S_C^*$ |   | CH |   | Is |
|---|---|---|---------|---|----|---|----|
| 6 | • | 84 | • | 85 | • | 208 | • |
| 7 | • | 95 | • | 100 | • | 191 | • |
| 8 | • | 94 | • | 109 | • | 188 | • |
| 9 | • | 95 | — | — | • | 191 | • |

TABLE 2

$(CH_3)_2CH-\overset{*}{C}H-COO-\phenyl-\phenyl-OOC-\phenyl-OC_nH_{2n+1}$
        |
        Cl

| n | K |   | $S_C^*$ |   | CH |   | Is |
|---|---|---|---------|---|----|---|----|
| 5 | • | 76 | • | 120 | • | 198 | • |
| 6 | • | 86 | • | 132 | • | 195 | • |
| 7 | • | 91 | • | 140 | • | 185 | • |
| 8 | • | 87 | • | 154 | • | 188 | • |
| 10 | • | 82 | • | 155 | • | 172 | • |
| 12 | • | 81 | • | 159$S_A$ | | 166.171 | • |

TABLE 3

$(CH_3)_2CH-\overset{*}{C}H-COO-G-X-B-Y-C-R^2$
        |
        Cl

| X | B | Y | C | $R^2$ | K | $S_B$ | $S_C$ | $S_A$ | CH | Is |
|---|---|---|---|-------|---|-------|-------|-------|----|----|
| —OOC— | phenyl | — | phenyl | $OC_8H_{17}$ | • 49 | — | • 58 | — | • 74[(1)] | • |

TABLE 3-continued $$(CH_3)_2CH-\overset{*}{\underset{Cl}{CH}}-COO-\underset{G}{\bigcirc}-X-\underset{B}{\bigcirc}-Y-\underset{C}{\bigcirc}-R^2$$

| X | B | Y | C | R² | K | S_B | S_C | S_A | CH | Is |
|---|---|---|---|----|---|-----|-----|-----|-----|-----|
| —COO— | biphenyl | —OOC— | phenyl | OC₅H₁₁ | • 180 | — | • 202 | — | • 340⁽²⁾ | • |
| —COO— | phenyl | — | pyrimidine | C₆H₁₃ | • 85 | — | — | — | • 149 | • |
| — | phenyl | —OOC | cyclohexyl | C₅H₁₁ | • 100 | • 156 | — | • 188 | • 215 | • |
| — | phenyl | —OOC | cyclohexyl | C₆H₁₃ | • 95 | • 151,5 | — | • 181 | • | |
| — | phenyl | —OOC | cyclohexyl | C₇H₁₅ | • | • | | | | |
| — | phenyl | —OOC | cyclohexyl | C₁₂H₂₅ | • 80 | • 149 | — | • 172–173 | — | • |
| — | phenyl | —OOC | phenyl | C₆H₁₃ | • 88 | •⁽³⁾ 93 | — | • 140 | — | • 172 | • |
| — | phenyl | —OOC | phenyl | CN | • 125 | — | — | • 173 | • 229 | • |
| — | phenyl | OOC | phenyl | C₆H₁₃ | • 88 | • 93 | • — | — 140 | • 172 | • |
| — | phenyl | OOC | phenyl | O—CH₂—CH=CH₂ | • 92 | — | • — | — 103 | • 204 | • |
| — | phenyl | OOC | phenyl | O—C₃H₇ | • 113 | — | • 155 | — | • 210 | • |

TABLE 3-continued $(CH_3)_2CH-\overset{*}{C}H(Cl)-COO-G-X-B-Y-C-R^2$

| X | B | Y | C | R² | K | S_B | S_C | S_A | CH | Is |
|---|---|---|---|---|---|---|---|---|---|---|
| — | ⬡ (phenyl) | ooC | ⬡ (phenyl) | O—C₄H₉ | • 106 | — | • 126 | — | • 211 | • |
| — | ⬡ (phenyl) | OOC | ⬡ (phenyl) | O—C₉H₁₉ | • 82 | — | • 152 | — | • 197 | • |

(1) Blue phase at 72–74° C.
(2) Decomposition
(3) $S_G$ phase, not $S_B$

TABLE 4

$(CH_3)_2CH-\overset{*}{C}H(Cl)-COO-\text{Ph}-\text{Pyr}-C_nH_{2n+1}$

| n | K |  | is |
|---|---|---|---|
| 7 | • | 60 | • |
| 9 | • | 45 | • |

TABLE 5

$(CH_3)_2CH-\overset{*}{C}H(Cl)-COO-\text{Ph}-COO-\text{Ph}-\text{Pyr}-C_nH_{2n+1}$

| n | K |  | S |  | CH |  | is |
|---|---|---|---|---|---|---|---|
| 7 | • | 70 | • | 96 | • | 202 | • |
| 9 | • | 62 | • | 69 | • | 157 | • |

TABLE 6

$(CH_3)_2CH-\overset{*}{C}H(Cl)-COO-\text{Ph}-\text{Ph}-COOR$

| R | K |  | S_C* |  | CH |  | is |
|---|---|---|---|---|---|---|---|
| —H | • | 222 | • | 240 | • | 260 | • |
| —Ph—OCOC₆H₁₃ | • | 130 | • | 150 | • |  | • |

TABLE 6-continued $(CH_3)_2CH-\overset{*}{C}H(Cl)-COO-\text{Ph}-\text{Ph}-COOR$

| R | K |  | S_C* |  | CH |  | is |
|---|---|---|---|---|---|---|---|
| —Ph—OCOC₇H₁₅ | • | 106 | • | 150 | • |  | • |

TABLE 7

$(CH_3)_2CH-CH_2-\overset{*}{C}H(Cl)-COO-\text{Ph}-OOC-\text{Ph}-OC_{10}H_{21}$

| K |  | S_C* |  | S_A |  | is |
|---|---|---|---|---|---|---|
| • | 44 | (• | 34) | • | 58 | • |

TABLE 8

$(CH_3)_2CH-CH_2-\overset{*}{C}H(Cl)-COO-\text{Ph}-\text{Ph}-OOC-\text{Ph}-OC_nH_{2n+1}$

| n | K |  | S_C* |  | S_A |  | CH |  | Is |
|---|---|---|---|---|---|---|---|---|---|
| 5 | • | 99 | • | 116 | — |  | • | 158 | • |
| 6 | • | 86 | • | 122 | • | 142 | • | 156 | • |
| 7 | • | 81 | • | 132 | • | 145 | • | 160 | • |

TABLE 8-continued
| n | K | | $S_C^*$ | | $S_A$ | | CH | | Is |
|---|---|---|---|---|---|---|---|---|---|
| 8 | • | 80–82 | • | 137 | • | 154 | • | 160 | • |
TABLE 9
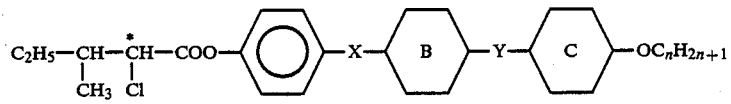
| X | B | Y | C | n | K | | $S_A$ | | CH | | Is |
|---|---|---|---|---|---|---|---|---|---|---|---|
| —OOC— | ⬡(phenyl) | — | — | 8 | • | 70 | (• | 48 | • | 63) | • |
| — | ⬡(phenyl) | —OOC— | ⬡(phenyl) | 8 | • | 94 | • | 174 | • | 187 | • |
| — | ⬡(phenyl) | —OOC— | ⬡(phenyl) | 10 | • | 76 | • | 141 | • | 166 | • |
| — | ⬡(phenyl) | —OOC— | ⬡(phenyl) | 12 | • | 90 | • | 159 | • | 190 | • |
| OOC | ⬡(phenyl) | — | — | 6 | • | 64 | (• | 42 | • | 45) | • |
| ooC | ⬡(phenyl) | — | — | 7 | • | 62 | (• | 33 | • | 38) | • |
| OOC | ⬡(phenyl) | — | — | 9 | • | 60 | • | 80 | — | — | • |
TABLE 10
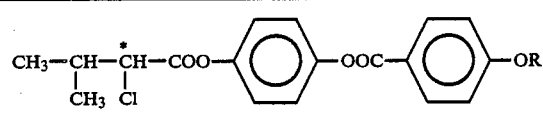
| R | K | | $S_C^*$ | $S_A$ | CH | Bl.Ph. | I |
|---|---|---|---|---|---|---|---|
| $C_5H_{11}$ | • | 92–93 | | | (• 64) | — | • |
| $C_6H_{13}$ | • | 87–88 | | | (• 58) | — | • |
| $C_7H_{15}$ | • | 74–75 | • (53,5) | | • 56) | (• 58) | • |
| $C_8H_{17}$ | • | 49 | • 58 | | • 72 | • 74 | • |
| $C_9H_{19}$ | • | 65 | • (46,5) | | • 57 | • 70 | • |
TABLE 10-continued
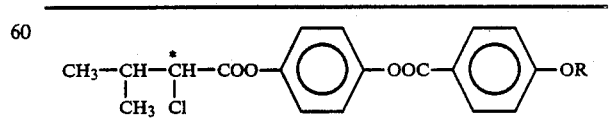
| R | K | | $S_C^*$ | $S_A$ | CH | Bl.Ph. | I |
|---|---|---|---|---|---|---|---|
| $C_{10}H_{21}$ | • | 66 | • (45) | • 68 | • 70 | • 72 | • |
| $C_{12}H_{25}$ | | 62–63 | • (42) | • 69 | — — | — — | • |

In the following Table 11, substances with their transition points are given. They were combined into different mixtures, the transition temperatures of which were then determined.

| Substance No. | | Transition Points | | | | T/°C. Blue Phase | Is |
|---|---|---|---|---|---|---|---|
| | | K | S$_C$* | S$_A$ | CH | | |
| 1 | 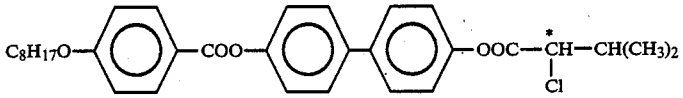 | • 90 | • 153 | — — | • 188 | — — | • |
| 2 | 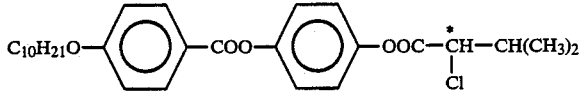 | • 66 | (• 45) | • 68 | • 70 | • 72 | • |
| 3 | 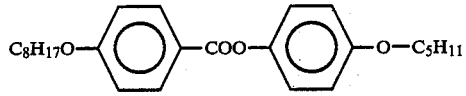 | • 38–39 | • 44 | • 60 | • 62.5 | — — | • |
| 4 | 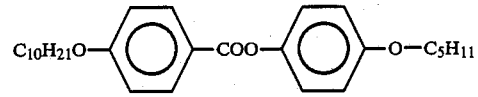 | • 40 | • 51 | • 65 | — — | — — | • |
| 5 | 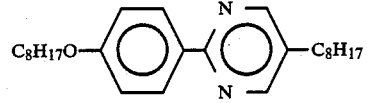 | • 28.5 | • 55.5 | • 62 | • 68 | — — | • |
| 6 | 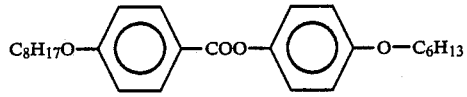 | • 55 | • 66 | — — | • 89.5 | — — | • |
| 7 | 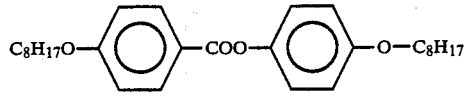 | • 62.5 | • 73.5 | — — | • 90.5 | — — | • |

Mixtures produced:

Mixture 1

The mixture consists of:

| | |
|---|---|
| No. 1 (S)-(+)-1-[4-n-octyloxybenzoyloxy]-4'-[2-chloro-3-methylbutyryloxy]-biphenyl | 25 mole % |
| No. 2 (S)-(+)-4-n-decyloxybenzoic-acid-4'-[2-chloro-3-methylbutyloxy]-phenyl ester | 75 mole % |

Mixture 2

The mixture consists of

| | |
|---|---|
| No. 1 (S)-(+)-1-[4-n-octyloxybenzoyloxy]-4'-[2-chloro-3-methylbutyryloxy]-biphenyl | 16.1 mole % |
| No. 2 (S)-(+)-4-n-decyloxybenzoic-acid-4-[2-chloro-3-methylbutyryloxy]-phenyl ester | 48.2 mole % |
| No. 3 (S)-4-n-octyloxybenzoic-acid-4-[2-methyl-butyloxy]-ester | 35.7 mole % |

Mixture 3

The mixture consists of

| | |
|---|---|
| No. 1 (S)-(+)-1-[4-n-octylbenzoyloxy]-4'-[2-chloro-3-methylbutyryloxy]-biphenyl | 23.75 mole % |
| No. 2 (S)-(+)-4-n-decyloxybenzoic-acid-4-[2-chloro-3-methylbutyryloxy]-phenyl ester | 71.25 mole % |
| No. 5 5-n-octyl-2-[4-n-octyloxy-phenyl]-pyrimidine | 5.00 mole % |

Mixture 4

The mixture consists of

| | |
|---|---|
| No. 1 (S)-(+)-1-[4-n-octyloxybenzoyloxy]-4'-[2-chloro-3-methylbutyryloxy]-biphenyl | 13.5 mole % |
| No. 2 (S)-(+)-4-n-decyloxybenzoic-acid-4'-[2-chloro-3-methylbutyryloxy]-phenyl ester | 25.3 mole % |
| No. 4 (S)-4-n-decyloxybenzoic-acid-4-[2-methyl-butyloxy]-phenyl ester | 61.2 mole % |

Mixture 5

The mixture consists of

| | |
|---|---|
| No. 1 (S)-(+)-1-[4-n-octylbenzoyloxy]-4'-[2-chloro-3-methylbutyryloxy]-biphenyl | 11.5 mole % |
| No. 2 (S)-(+)-4-n-decyloxy-benzoic-acid-4-[2-chloro-3-methylbutyryloxy]-phenyl ester | 21.5 mole % |
| No. 4 (S)-4-n-decyloxy-benzoic-acid-4-[2-methyl-butyloxy]-phenyl ester | 52 mole % |
| No. 5 5-n-octyl-2-[4-n-octyloxy-phenyl]-pyrimi- | 15 mole % |

Mixture 6

The mixture consists of

| | | |
|---|---|---|
| No. 1 | (S)-(+)-1-[4-n-octylbenzoyloxy]-4'-[2-chloro-3-methylbutyryloxy]-biphenyl | 5 mole % |
| No. 3 | (S)-4-n-octyloxy-benzoic-acid-4-[2-methyl-butyloxy]-phenyl ester | 56 mole % |
| No. 6 | 4-n-octyloxy-benzoic-acid-4-n-hexyloxy-phenyl ester | 22.8 mole % |
| No. 7 | 4-n-octyloxy-benzoic-acid-4-n-octylphenyl ester | 16.2 mole % |

Mixture 7

The mixture consists of

| | | |
|---|---|---|
| No. 2 | (S)-(+)-4-n-decyloxybenzoic-acid-4-[2-chloro-3-methylbutyryloxy]-phenyl ester | 10 mole % |
| No. 3 | (S)-4-n-octyloxybenzoic-acid-4-[2-methyl-butyloxy]-phenyl ester | 53 mole % |
| No. 6 | 4-n-octylbenzoic-acid-4-n-hexyloxyphenyl ester | 21.6 mole % |
| No. 7 | 4-n-octylbenzoic-acid-4-n-octyloxyphenyl ester | 15.3 mole % |

Mixture 8

The mixture consists of

| | | |
|---|---|---|
| No. 1 | (S)-(+)-1-[4-n-octylbenzoyloxy]-4'-[2-chloro-3-methylbutyryloxy]-biphenyl | 9.5 mole % |
| No. 2 | (S)-(+)-4-n-decyloxybenzoic-acid-4-[2-chloro-3-methylbutyryloxy]-(S)-(+)-phenyl ester | 17.67 mole % |
| No. 4 | (S)-4-n-decyloxybenzoic-acid-4-[2-methyl-butyloxy]-phenyl ester | 42.79 mole % |
| No. 6 | 4-n-octyloxybenzoic-acid-4-n-hexyloxyphenyl ester | 17.5 mole % |
| No. 7 | 4-n-octyloxybenzoic-acid-4-n-octyloxyphenyl ester | 12.45 mole % |

| Transition Temperatures of the Mixtures Mixture Transition Points | | | | | | | | | | | |
|---|---|---|---|---|---|---|---|---|---|---|---|
| | K | | $S_C$ | | $S_A$ | | CH | | Blue Phase | | Is |
| 1 | • 23 | • | 63 | • | 86,5 | • | 92 | • | 100 | | • |
| 2 | • 18 | • | 45 | • | 75 | • | 89 | — | — | | • |
| 3 | • 24 | • | 58 | • | 85,5 | • | 90,5 | • | 96,5 | | • |
| 4 | • 21 | • | 52 | • | 77 | • | 82 | — | — | | • |
| 5 | • 15 | • | 39 | • | 70 | • | 76 | — | — | | • |
| 6 | • 17,5 | • | 55 | • | 66 | • | 79,5 | — | — | | • |
| 7 | • 17 | • | 48 | • | 68 | • | 74 | — | — | | • |
| 8 | • 28 | • | 54 | • | 76 | • | 81,5 | — | — | | • |

All mixtures have ferroelectric phases, which are stable at room temperature or at somewhat higher temperatures.

We claim:

1. Liquid crystalline ferroelectric compounds of the formula

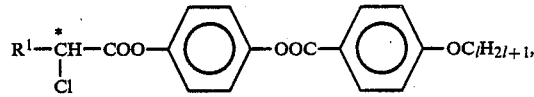

wherein $R^1$ is $(CH_3)_2CH-$, $(CH_3)_2CHCH_2-$ or $C_2H_5CH(CH_3)-$ and $l$ is an integer 1 to 12.

2. Liquid crystalline ferroelectric compounds as defined in claim 1, in which $R^1$ is $C_2H_5CH(CH_3)$.

3. A liquid crystalline ferroelectric compound as defined in claim 1, in which $R^1$ is $(CH_3)_2CH-$ and $l$ is 10.

4. Liquid crystalline ferroelectric compounds as defined in claim 1, in which $R_1$ is $(CH_3)_2CH-$.

5. In an opto-electronic display containing at least one liquid crystal compound, the improvement in which at least one of said compounds is according to claim 2.

6. In an opto-electronic display containing at least one liquid crystal compound, the improvement in which at least one of said compounds is according to claim 1.

7. In an opto-electronic display containing at least one liquid crystal compound, the improvement in which at least one of said compounds is according to claim 3.

8. In an opto-electronic display containing at least one liquid crystal compound, the improvement in which at least one of said compounds is according to claim 4.

* * * * *